(12) United States Patent
Zhang et al.

(10) Patent No.: US 12,426,834 B2
(45) Date of Patent: Sep. 30, 2025

(54) UNLOCKING METHOD AND INTELLIGENT LOCK BASED ON VEIN INPUT AND IDENTIFICATION

(71) Applicant: IDLESPACE TECHNOLOGY COMPANY CO., LTD, Seattle, WA (US)

(72) Inventors: Gang Zhang, Seattle, WA (US); Qiyun Su, Seattle, WA (US); Xian Li, Seattle, WA (US)

(73) Assignee: IDLESPACE TECHNOLOGY COMPANY CO., LTD, Seattle, WA (US)

( * ) Notice: Subject to any disclaimer, the term of this patent is extended or adjusted under 35 U.S.C. 154(b) by 43 days.

(21) Appl. No.: 18/431,053

(22) Filed: Feb. 2, 2024

(65) Prior Publication Data

US 2025/0057474 A1    Feb. 20, 2025

(30) Foreign Application Priority Data

Aug. 15, 2023   (CN) .......................... 202311031438.1

(51) Int. Cl.
| | |
|---|---|
| *A61B 5/00* | (2006.01) |
| *G06T 7/00* | (2017.01) |
| *G06T 7/13* | (2017.01) |
| *G16H 50/20* | (2018.01) |

(52) U.S. Cl.
CPC ............ *A61B 5/489* (2013.01); *G06T 7/0016* (2013.01); *G06T 7/13* (2017.01); *G16H 50/20* (2018.01); *G06T 2207/30101* (2013.01)

(58) Field of Classification Search
None
See application file for complete search history.

(56) References Cited

U.S. PATENT DOCUMENTS

| | | | | |
|---|---|---|---|---|
| 2010/0128927 A1* | 5/2010 | Ikenoue | ............... | G06V 40/167 |
| | | | | 382/199 |
| 2025/0005981 A1* | 1/2025 | Qian | .................. | G07C 9/00944 |

* cited by examiner

*Primary Examiner* — Clifford Hilaire
(74) *Attorney, Agent, or Firm* — Maier & Maier, PLLC (57) ABSTRACT

An unlocking method and an intelligent lock based on vein input and identification. The method includes steps of obtaining positional information of a target part, adjusting a position of the target part to be within a preset position-identification range, inputting a vein image of the target part to be within the position-identification range, where the vein image includes a first vein image and a second vein image; processing the input first vein image to obtain a first vein feature of the first vein image, constructing a feature map based on the first vein feature; processing the input second vein image to obtain a second vein feature of the second vein image, comparing the second vein feature with the first vein feature of the feature map to obtain a comparison result, and determining an unlocking state based on the comparison result.

8 Claims, 6 Drawing Sheets

FIG. 7

UNLOCKING METHOD AND INTELLIGENT LOCK BASED ON VEIN INPUT AND IDENTIFICATION

CROSS-REFERENCES TO RELATED APPLICATIONS

This application claims priority to Chinese Patent Application No. 202311031438.1, filed on Aug. 15, 2023, the content of all of which is incorporated herein by reference.

FIELD

The present disclosure relates to the technical field of intelligent locks, in particular to an unlocking method and an intelligent lock based on vein input and identification.

BACKGROUND

In the prior art, biometric identification technology has gradually replaced traditional identity authentication modes such as magnetic cards, passwords, etc., effectively avoiding the risk of loss and theft of the traditional identity authentication modes, and improving the security and convenience of identity authentication. The biometric identification technology uses the inherent physiological characteristics and behavioral features of human body, combined with technologies such as optics, acoustics, sensor, pattern matching, deep learning, etc. to achieve identifying personal identity. The biometric identification technology mainly includes face identification, fingerprint identification, voiceprint identification, iris identification, etc.

However, the face identification is not complex enough and is easily affected by external environments; the fingerprint identification is easily forged and copied, easily affected by external environments, easily affected by skin surface conditions, and difficult for people with unclear fingerprints such as the elderly and children; the voiceprint identification has low accuracy and faces sound recording and wiretapping; the iris identification is difficult to collect and has limited usage. That is, the existing biometric identification technology cannot meet the security and convenience required during the identification process.

Therefore, the prior art still needs to be improved.

SUMMARY

The present disclosure provides an unlocking method and an intelligent lock based on vein input and identification in view of the above-mentioned defects of the prior art, aiming to solve the following technical problem: in the prior art, the face identification is not complex enough and is easily affected by external environments; the fingerprint identification is easily forged and copied, easily affected by external environments, easily affected by skin surface conditions, and difficult for people with unclear fingerprints such as the elderly and children; the voiceprint identification has low accuracy and faces sound recording and wiretapping; the iris identification is difficult to collect and has limited usage; that is, the existing biometric identification technology cannot meet the security and convenience required during the identification process.

In order to solve the above-mentioned technical problem, the technical schemes adopted by the present disclosure are as follows:

In a first aspect, the present disclosure provides an unlocking method based on vein input and identification, and the method includes steps of:

obtaining positional information of a target part, adjusting a position of the target part to be within a preset position-identification range, and inputting a vein image of the target part to be within the preset position-identification range, where the vein image includes a first vein image and a second vein image;

processing the input first vein image to obtain a first vein feature of the first vein image, and constructing a feature map based on the first vein feature; and processing the input second vein image to obtain a second vein feature of the second vein image, comparing the second vein feature with the first vein feature of the feature map to obtain a comparison result, and determining an unlocking state based on the comparison result.

In one implementation, the vein image of the target part is one or more of a palm vein image, a finger vein image, and/or a wrist vein image.

In one implementation, the step of obtaining the positional information of the target part, adjusting the position of the target part to be within the preset position-identification range, includes steps of:

receiving an input command, and collecting an original image of the target part based on the input command;

performing a binarization processing and an edge detection on the original image to obtain an image contour of the target part in the original image, and determining a center-point position of the target part based on the image contour; and adjusting the position of the target part to be within the preset position-identification range based on the center-point position.

In one implementation, the step of adjusting the position of the target part to be within the preset position-identification range based on the center-point position, includes steps of:

dividing the preset position-identification range into a plurality of areas, and determining an area where the center-point position is located;

based on the area where the center-point position is located, calculating area offset information of the area relative to a center of the preset position-identification range; and based on the area offset information, controlling an angle control unit to adjust an identification angle of an adjustable support to make the area where the center-point position is located be at the center of the preset position-identification range.

In one implementation, the step of inputting the vein image of the target part to be within the preset position-identification range, where the vein image includes the first vein image and the second vein image, includes steps of:

reading an input mode, and determining a type of the vein image of the input target part;

when the input mode is a registration mode, determining the vein image of the input target part as the first vein image; and when the input mode is an identification mode, determining the vein image of the input target part as the second vein image.

In one implementation, the step of processing the input first vein image to obtain the first vein feature of the first vein image, and constructing the feature map based on the first vein feature, includes steps of:

segmenting the first vein image to divide the first vein image into a plurality of feature areas;

extracting and calculating first vein information of each feature area, where the first vein information includes a vein path position, bifurcation-point information, trend information, and ending information; and recording valid information of the first vein information, and constructing the feature map based on the valid information.

In one implementation, the step of comparing the second vein feature with the first vein feature of the feature map to obtain the comparison result, and determining the unlocking state based on the comparison result, includes steps of:

comparing second vein information of the second vein feature respectively with the first vein information of the first vein feature of the feature map to obtain a comparison score;

if the comparison score is less than a preset score, controlling a latch drive unit to maintain a locked state; and if the comparison score is greater than the preset score, controlling the latch drive unit to unlock.

In a second aspect, the embodiments of the present disclosure further provide an intelligent lock based on vein input and identification, and the intelligent lock includes:

a vein image input module, configured to obtain positional information of a target part, adjust a position of the target part to be within a preset position-identification range, and input a vein image of the target part to be within the preset position-identification range, where the vein image includes a first vein image and a second vein image;

a feature map construction module, configured to process the input first vein image to obtain a first vein feature of the first vein image, and construct a feature map based on the first vein feature; and an unlocking state determination module, configured to process the input second vein image to obtain a second vein feature of the second vein image, compare the second vein feature with the first vein feature of the feature map to obtain a comparison result, and determine an unlocking state based on the comparison result.

In a third aspect, the embodiments of the present disclosure further provide a terminal device, and the terminal device includes a memory, a processor, and an unlocking program based on vein input and identification; the unlocking program is stored in the memory and executable on the processor; when the unlocking program is executed by the processor, the steps of the above-mentioned unlocking method based on vein input and identification are implemented.

In a fourth aspect, the embodiments of the present disclosure further provide a computer-readable storage medium, and an unlocking program based on vein input and identification is stored in the computer-readable storage medium; when the unlocking program is executed by a processor, the steps of the above-mentioned unlocking method based on vein input and identification are implemented.

Beneficial effects: compared with the prior art, the present disclosure provides an unlocking method based on vein input and identification. First, the positional information of the target part is obtained, the position of the target part is adjusted to be within the preset position-identification range, the vein image of the target part is input within the position-identification range, and the vein image includes the first vein image and the second vein image. The input first vein image is processed to obtain the first vein feature of the first vein image, and the feature map is constructed based on the first vein feature. The input second vein image is processed to obtain the second vein feature of the second vein image, the second vein feature is compared with the first vein feature of the feature map to obtain the comparison result, the unlocking state based on the comparison result is determined. In the present disclosure, vein features are used as an identification basis for unlocking, therefore, the unlocking method based on vein input and identification provided by the present disclosure can improve the security and accuracy when authenticating a user's identity.

DETAILED DESCRIPTION OF EMBODIMENTS

In order to make the purposes, technical schemes and effects of the present disclosure clearer and more explicit, the present disclosure is further described in detail below with reference to the accompanying drawings and embodiments.

Those skilled in the art should understand that the specific embodiments described here are only used to explain the present disclosure and are not intended to limit the present disclosure. Unless specifically stated, the singular forms "a", "an", "said", and "the" used herein may also include the plural form. The terms "comprise" and "include" used in the specification of the present disclosure refer to the presence of stated features, integers, steps, operations, elements and/or components, but do not exclude the presence or addition of one or more other features, integers, steps, operations, elements, components, and/or groups thereof. It should be understood that when an element is referred to being "connected" or "coupled" to another element, the element may be directly connected or coupled to another element or intervening elements may further be present. Additionally, "connected" or "coupled" as used herein may include a wireless connection or a wireless coupling. As used herein, the term "and/or" includes all or any one unit and all combinations of one or more of the associated listed items.

The present embodiment provides an unlocking method based on vein input and identification. During an implementation, in the present embodiment, first positional information of a target part is obtained, a position of the target part is adjusted to be within a preset position-identification range, a vein image of the target part is input to be within the position-identification range, and the vein image includes a first vein image and a second vein image. Second, the input first vein image is processed to obtain a first vein feature of the first vein image, and a feature map is constructed based on the first vein feature. Third, the input second vein image is processed to obtain a second vein feature of the second vein image, the second vein feature is compared with the first vein feature of the feature map to obtain a comparison result, an unlocking state based on the comparison result is determined. The present embodiment can improve the security and accuracy of an identity authentication of a user by using vein features as an identification basis for unlocking.

Exemplary Method

Figure 1:
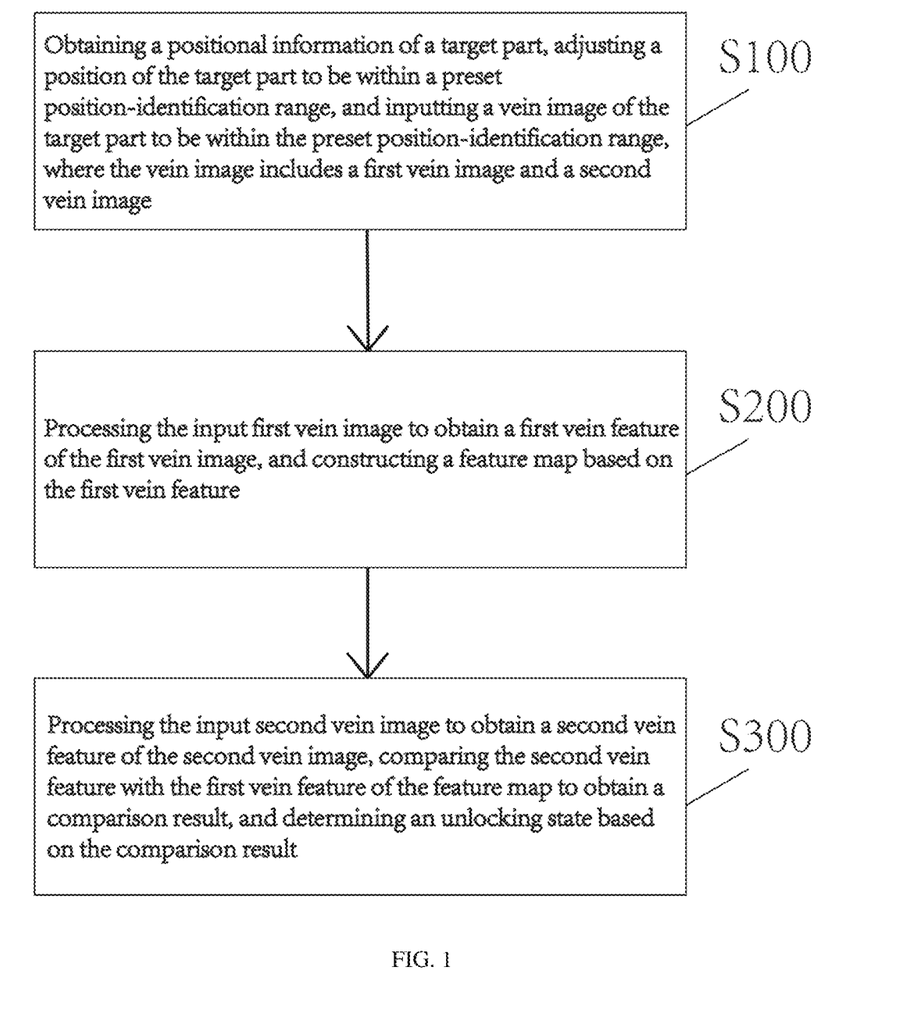
FIG. 1 is a flow chart of an implementation of an unlocking method based on vein input and identification provided by the embodiments of the present disclosure.

The unlocking method based on vein input and identification in the present embodiment can be applied to a terminal device, the terminal device may be a preset mobile terminal such as a mobile phone, a tablet, a computer, etc., or may also be an intelligent device such as an intelligent TV. In the present embodiment, the terminal device may be an external device connected to an intelligent lock based on vein input and identification, or may be a device built in the intelligent lock based on vein input and identification. As shown in FIG. 1, the unlocking method based on vein input and identification in the present embodiment includes following steps.

Step S100, obtaining a positional information of a target part, adjusting a position of the target part to be within a preset position-identification range, and inputting a vein image of the target part to be within the position-identification range, where the vein image includes a first vein image and a second vein image.

Since the present embodiment uses a vein feature of the input vein image as an identification basis of unlocking information, the present embodiment first needs to collect and input the vein image of the target part. In order to obtain comprehensive vein features, the present embodiment needs to obtain a complete vein image, that is, to obtain the positional information of the target part, adjust the position of the target part to be within the preset position-identification range, and then input the vein image of the target part to be within the preset position-identification range, so as to collect and input the complete vein image.

In one implementation, the vein image of the target part in the present embodiment is one or more of a palm vein image, a finger vein image, and/or a wrist vein image.

In one implementation, the intelligent lock based on vein input and identification in the present embodiment may use any one of a palm, a finger, and a wrist as the target part for identification, and there is no specific limitation on the target part in the present embodiment. Correspondingly, the vein image of the target part in the present embodiment is one or more of the group consisting of the palm vein image, the finger vein image, and the wrist vein image.

Figure 2:
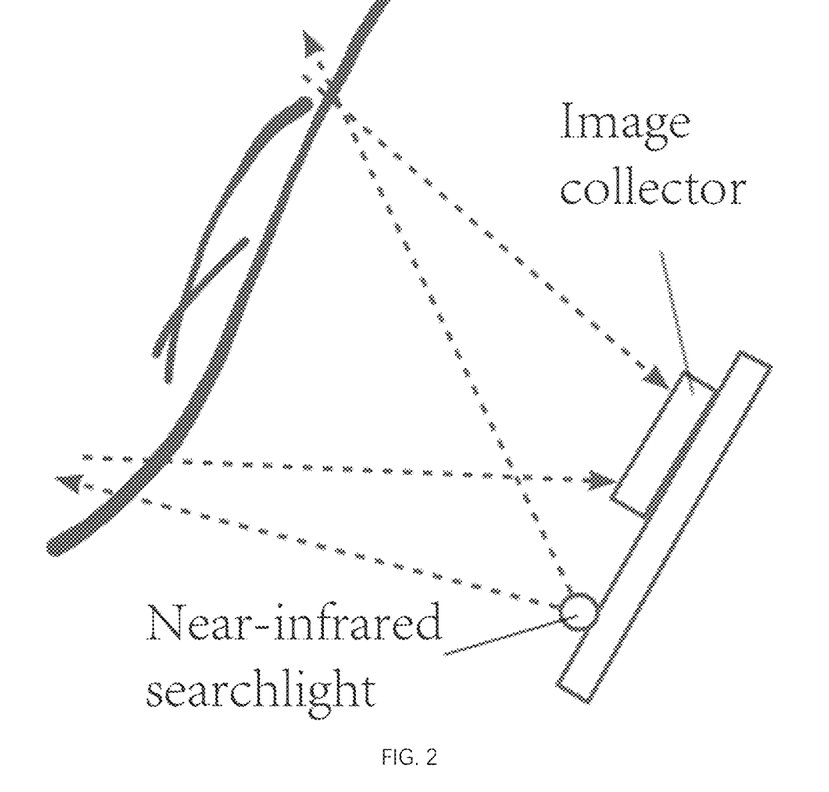
FIG. 2 is a schematic diagram of a palm vein image identification method provided by the embodiments of the present disclosure.

When the input vein image of the target part is a palm vein image, the palm vein identification method in the present embodiment is as shown in FIG. 2. The intelligent lock in the present embodiment may collect a palm vein feature through a near-infrared searchlight, and store the collected palm vein feature in an image collector. Vein identification uses strength of a reflected near-infrared ray to identify distribution and positional information of a vein. When using the near-infrared searchlight to illuminate a palm, a sensor senses the light reflected by the palm, at the same time, hemoglobin flowing in venous red blood cell absorbs a near-infrared ray having a wavelength near 760 nm, resulting in less reflection of the vein, so that a vein pattern is generated on image, and the vein pattern generated at this time is stored in the image collector.

Figure 3:
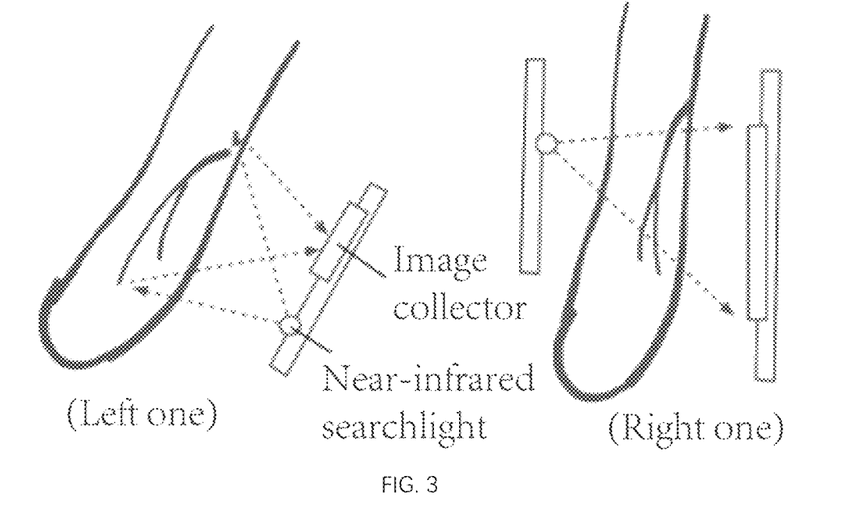
FIG. 3 is a schematic diagram of a finger vein image identification method provided by the embodiments of the present disclosure.

When the input vein image of the target part is a finger vein image, as shown in FIG. 3, there are two finger vein identification methods, which are a reflective identification method (left one in FIG. 3) and an opposed identification method (right one in FIG. 3). In the reflective identification method, a near-infrared searchlight and an image collector of the intelligent lock of the present embodiment are placed at the same side of the finger, a finger vein feature is collected by the near-infrared searchlight, and the collected finger vein feature is stored in the image collector. In the opposed identification method, a near-infrared searchlight and an image collector are placed at two sides of the finger in the above-mentioned intelligent lock, the near-infrared searchlight illuminates light passing through the finger, and the light passing through the finger is entered in the image collector for identification and storage.

In one implementation, the vein identification method in the present embodiment is a non-contact sensing method. The non-contact vein identification method can reduce indirect contact between different users, making the unlocking method of the present embodiment more hygienic and improving the user's sense of use.

In one implementation, in the present embodiment, the step of obtaining the positional information of the target part, adjusting the position of the target part to be within the preset position-identification range, includes the following steps:

Step S101, receiving an input command, and collecting an original image of the target part based on the input command;

Step S102, performing a binarization processing and an edge detection on the original image to obtain an image contour of the target part in the original image, and determining a center-point position of the target part based on the image contour;

Step S103, adjusting the position of the target part to be within the preset position-identification range based on the center-point position.

Figure 4:
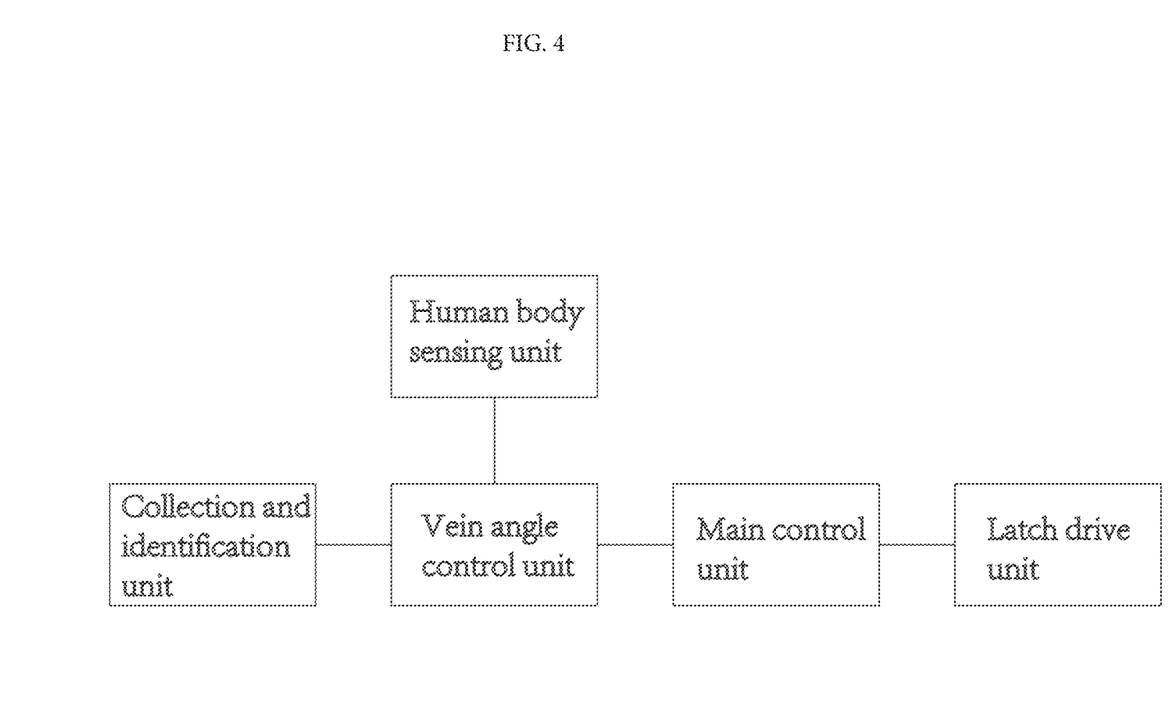
FIG. 4 is a framework diagram of a vein door lock system provided by the embodiments of the present disclosure.

In one implementation, as shown in FIG. 4, a framework of a vein door lock system of the present embodiment includes five units: a human body sensing unit, a collection and identification unit, a vein angle control unit, a main control unit, and a latch drive unit. When the human body sensing unit in the intelligent lock of the present embodiment senses that someone is approaching, for example, when a distance between the human body and the intelligent lock is 5~100 cm, the input command is triggered. When the intelligent lock of the present embodiment receives the input command, the vein collection and identification unit is started to collect the original image of the target part. The target part in the present embodiment is described below using a palm as an example. When collecting the original image of the palm based on the input command, the user puts the palm in the vein collection and identification unit of the intelligent lock, the vein collection and identification unit first collects the original image of the palm, and then performs the binarization processing based on the original image. The binarization processing is to set grayscale of points on image to 0 or 255, that is, the grayscale image with 256 brightness levels is selected by an appropriate threshold to obtain a binarization image, and the binarization image can still reflect overall and local features of image, and has an obvious black and white effect. After the binarization processing, the present embodiment can obtain a contour of the palm, and distinguish the contour of the palm in the original image from a background in the original image. In one implementation, in the present embodiment, an edge detection is performed on the original image in order to facilitate dividing areas and positions of the original image.

Furthermore, the vein collection and identification unit of the present embodiment determines the center-point position of the target part based on the obtained contour of the palm after processing, that is, the center-point position of the target part is a palm-center position. In order to more quickly adjust the position of the target part to be within the preset position-identification range, in the present embodiment, the center-point position of the target part is used as a reference center during adjustment. That is to say, in the present embodiment, a position of the palm is adjusted to be within the preset position-identification range based on the palm-center position, so that the position of the palm is adjusted to optimal position-identification range more quickly.

In one implementation, step S103 of the present embodiment includes the following steps:

Step S1, dividing the preset position-identification range into a plurality of areas, and determining an area where the center-point position is located;

Step S2, calculating an area offset information of the area relative to a center of the preset position-identification range based on the area where the center-point position is located;

Step S3, based on the area offset information, controlling an angle control unit to adjust an identification angle of an adjustable support to make the area where the center-point position is located be at a center of the preset position-identification range.

Figure 5:
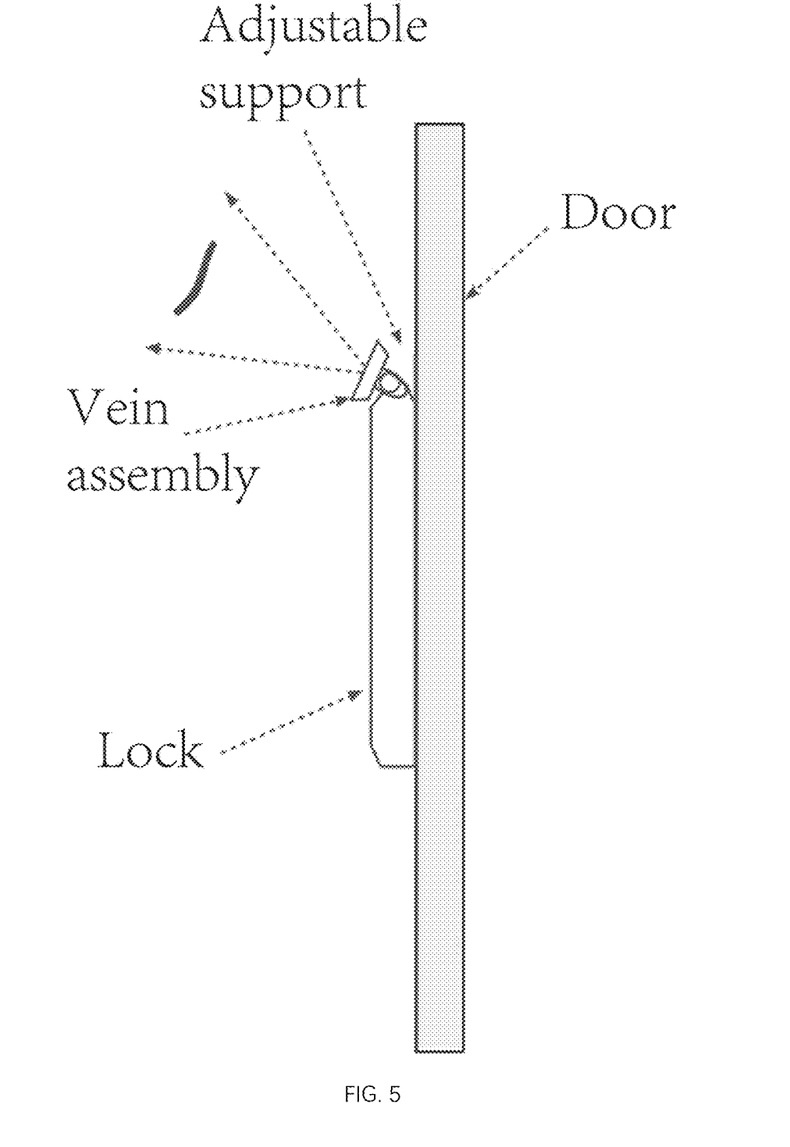
FIG. 5 is a schematic diagram of an installation position of an adjustable support provided by the embodiments of the present disclosure.

In one implementation, in the present embodiment, first the preset position-identification range is divided into a plurality of areas. For example, when the preset position-identification range is a rectangle, based on two diagonal lines of the rectangle, the rectangle is divided into four areas: a top window area, a bottom window area, a left window area, and a right window area. Then, after the step of determining the center-point position of the target part based on the image contour, the present embodiment further determines which area of the preset position-identification range the center-point position is located in, and calculates an area offset information of the area relative to a center of the preset position-identification range based on the area where the center-point position is located, among them, the center of the preset position-identification range is an intersection-point position of the two diagonal lines. In addition, in the present embodiment, when the vein collection and identification unit collects the original image of the target part, the specific positional information in the original image can be accurately collected. Based on the specific positional information, the area offset information of the area where the center-point position is located relative to the center of the preset position-identification range, can be calculated through image operation. For example, an actual distance information between the palm-center position and the top window frame, an actual distance information between the palm-center position and the bottom window frame, an actual distance information between the palm-center position and the left window frame, and an actual distance information between the palm-center position and the right window frame can be calculated. Then, based on the actual distance information, the vein angle control unit is controlled to adjust an identification angle of an adjustable support to make the area where the center-point position is located be in the center of the preset position-identification range, among them, an installation location of the adjustable support in the vein identification component is shown in FIG. 5.

In one implementation, in the present embodiment, the step of inputting the vein image of the target part to be within the position-identification range, where the vein image includes the first vein image and the second vein image, includes the following steps:

Step S111, reading an input mode, determining a type of the vein image of the input target part;

Step S112, when the input mode is a registration mode, determining the vein image of the input target part as the first vein image;

Step S113, when the input mode is an identification mode, determining the vein image of the input target part as the second vein image.

In one implementation, in the intelligent lock of the present embodiment, when inputting the type of the vein image of the target part, the input mode is first read and whether the current input mode is the registration mode or the identification mode is determined. When the input mode is the registration mode, it is determined that the vein image of the input target part is the first vein image, a feature of the first vein image does not exist on the intelligent lock before registration, at this time, the user needs to register the input vein feature. When the input mode is the identification mode, it is determined that the vein image of the input target part is the second vein image, and the second vein image is configured to determine whether the user's vein feature is the same as previously registered vein feature.

Step S200, processing the input first vein image to obtain a first vein feature of the first vein image, and constructing a feature map based on the first vein feature.

When the input mode is the registration mode, in the present embodiment, the first vein feature of the currently input first vein image is extracted, the feature map based on the first vein feature is constructed, and then the feature map is stored in a vein feature database, facilitating that in subsequent identification mode there is a vein feature database for reference when matching identity information of user.

In one implementation, step S200 of the present embodiment includes the following steps:

Step S201, segmenting the first vein image to divide the first vein image into a plurality of feature areas;

Step S202, extracting and calculating a first vein information of each feature area, where the first vein information includes a vein path position, a bifurcation-point information, a trend information, and an ending information;

Step S203, recording a valid information of the first vein information, and constructing the feature map based on the valid information.

In one implementation, in the present embodiment, the process of processing the input first vein image is mainly divided into image segmentation and feature extraction. The target part in the present embodiment is described below using a palm as an example. In the present embodiment, first, the input first vein image of the palm is segmented to divide the first vein image into a plurality of feature areas. For example, the first vein image may be divided into 4, 9, or 16 feature areas by evenly segmenting the entire first vein image, or the first vein image may be divided by segmenting different parts of the palm which is not specifically limited in the present embodiment. Then, the first vein information of each feature area is extracted and calculated, the first vein information includes the vein path position, the bifurcation-point information, the trend information, the ending information, etc., among them, the calculation thereof includes an image enhancement and an image correction. Through the image enhancement and the image correction, the accuracy of the extracted vein information of each feature area can be improved. Then, whether the feature area is a valid area or an invalid area is determined based on the calculation result and the extracted feature information. The invalid area may be caused by unclear image collection and other reasons. Then, the effective information of the vein information such as the vein path position, the bifurcation-point information, the trend information, the ending information, etc. of each feature area is recorded to construct the feature map. Therefore, the feature map also has multiple feature areas.

Step S300, processing the input second vein image to obtain a second vein feature of the second vein image, comparing the second vein feature with the first vein feature of the feature map to obtain a comparison result, and determining an unlocking state based on the comparison result.

In one implementation, the embodiment processes the input second vein image in the same manner as the first vein image. After processing to obtain the second vein feature, by comparing the second vein feature with the first vein feature of the feature map, the unlocking state can be determined. That is to say, the first vein feature is configured to register identity information of user and provide comparison parameters when unlocking, while the second vein feature is configured to match the identity information of the user and determine the final unlocking state.

In one implementation, in the present embodiment, the step of comparing the second vein feature with the first vein feature of the feature map to obtain the comparison result, and determining the unlocking state based on the comparison result, includes the following steps:

Step S301, comparing a second vein information of the second vein feature with the first vein information of the first vein feature of the feature map to obtain a comparison score;

Step S302, if the comparison score is less than a preset score, controlling the latch drive unit to maintain a locked state;

Step S303, if the comparison score is greater than the preset score, controlling the latch drive unit to unlock.

In one implementation, in the present embodiment, the final unlocking state is determined based on the comparison score obtained by comparing the second vein information with the first vein information. Since the feature map also has multiple feature areas, in the present embodiment, the second vein information of each feature area in the second vein feature is separately compared with the first vein information of multiple feature areas in the first vein feature of the feature map, so as to obtain the comparison scores. The preset score in the present embodiment can be set by a user. For example, when four feature areas are divided, the preset score may be that comparison similarities of the four feature areas are all greater than 90%. The comparison score is less than the preset score, that is, in the comparison similarities between the second vein information and the first vein information, there is at least one feature area with a comparison similarity less than 90%, then the identity information of the user is identified as failed and the latch drive unit is controlled to maintain a locked state. The comparison score is greater than the preset score, that is, in the comparison similarities between the second vein information and the first vein information, the comparison similarities of the four feature areas are all greater than 90%, then the identity information of the user is identified as success and the latch drive unit is controlled to unlock.

In summary, the present embodiment provides an unlocking method based on vein input and identification. The method includes: first obtaining a positional information of a target part, adjusting a position of the target part to be within a preset position-identification range, and inputting a vein image of the target part to be within the position-identification range, where the vein image includes a first vein image and a second vein image; then processing the input first vein image to obtain a first vein feature of the first vein image, and constructing a feature map based on the first vein feature; then, processing the input second vein image to obtain a second vein feature of the second vein image, comparing the second vein feature with the first vein feature of the feature map to obtain a comparison result, and determining an unlocking state based on the comparison result. The present embodiment uses vein features as an identification basis for unlocking, thus the unlocking method based on vein input and identification provided by the present embodiment can improve the security and accuracy of a user's identity authentication.

Exemplary Apparatus

Figure 6:
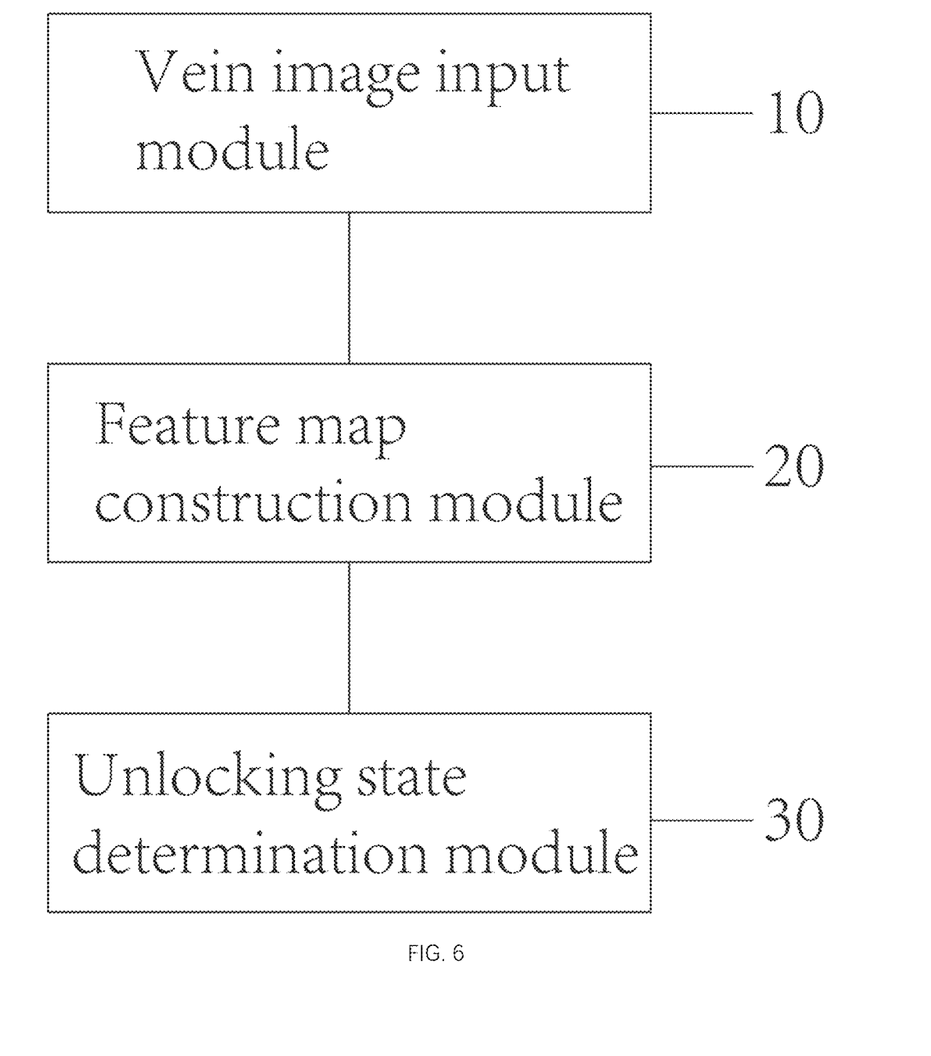
FIG. 6 is a functional principle diagram of an intelligent lock based on vein input and identification provided by the embodiments of the present disclosure.

Based on the above embodiments, the present disclosure further provides an intelligent lock based on vein input and identification. As shown in FIG. 6, the intelligent lock includes a vein image input module 10, a feature map construction module 20, and an unlocking state determination module 30. The vein image input module 10 is used to obtain a positional information of a target part, adjust a position of the target part to be within a preset position-identification range, and input a vein image of the target part to be within the preset position-identification range, where the vein image includes a first vein image and a second vein image. The feature map construction module 20 is used to process the input first vein image to obtain a first vein feature of the first vein image, and construct a feature map based on the first vein feature. The unlocking state determination module 30 is used to process the input second vein image to obtain a second vein feature of the second vein image, compare the second vein feature with the first vein feature of the feature map to obtain a comparison result, and determine an unlocking state based on the comparison result.

In one implementation, the vein image input module 10 includes:

A vein image determination unit, which is configured to include one or more of a palm vein image, a finger vein image, and a wrist vein image.

An original image collection unit, which is configured to receive an input command, and collect an original image of a target part based on the input command;

A center-point position determination unit, which is configured to perform a binarization processing and an edge detection on the original image to obtain an image contour of the target part in the original image, and determine a center-point position of the target part based on the image contour;

A target part position adjustment unit, which is configured to adjust the position of the target part to be within a preset position-identification range based on the center-point position.

A vein image type determination unit, which is configured to read an input mode, and determine a type of the vein image of the input target part;

A first vein image determination unit, which is configured to determine the vein image of the input target part as a first vein image when the input mode is a registration mode; and A second vein image determination unit, which is configured to determine the vein image of the input target part as a second vein image when the input mode is an identification mode.

In one implementation, the target part position adjustment unit includes:

an area division subunit, which is configured to divide the preset position-identification range into a plurality of areas, and determine an area where the center-point position is located;

an area offset information calculation subunit, which is configured to calculate an area offset information of the area relative to a center of the preset position-identification range based on the area where the center-point position is located; and an identification angle adjustment subunit, which is configured to control an angle control unit to adjust an identification angle of an adjustable support based on the area offset information, so as to make the area where the center-point position is located be at the center of the preset position-identification range.

In one implementation, the feature map construction module 20 includes:

a feature area division unit, which is configured to segment the first vein image to divide the first vein image into a plurality of feature areas;

an area information calculation unit, which is configured to extract and calculate a first vein information of each feature area, where the first vein information includes a vein path position, a bifurcation-point information, a trend information, and an ending information; and a feature map construction unit, which is configured to record a valid information of the first vein information, and construct a feature map based on the valid information.

In one implementation, the unlocking state determination module 30 includes:

a comparison score collection unit, which is configured to compare a second vein information of a second vein feature respectively with the first vein information of the first vein feature in the feature map to obtain a comparison score;

a locking determination unit, which is configured to control a latch drive unit to maintain a locked state if the comparison score is less than a preset score; and an unlocking determination unit, which is configured to control the latch drive unit to unlock if the comparison score is greater than the preset score.

Working principles of each module in the intelligent lock based on vein input and identification in the present embodiment are the same as the principles of each step in the above method embodiments, and are not described again here.

Figure 7:
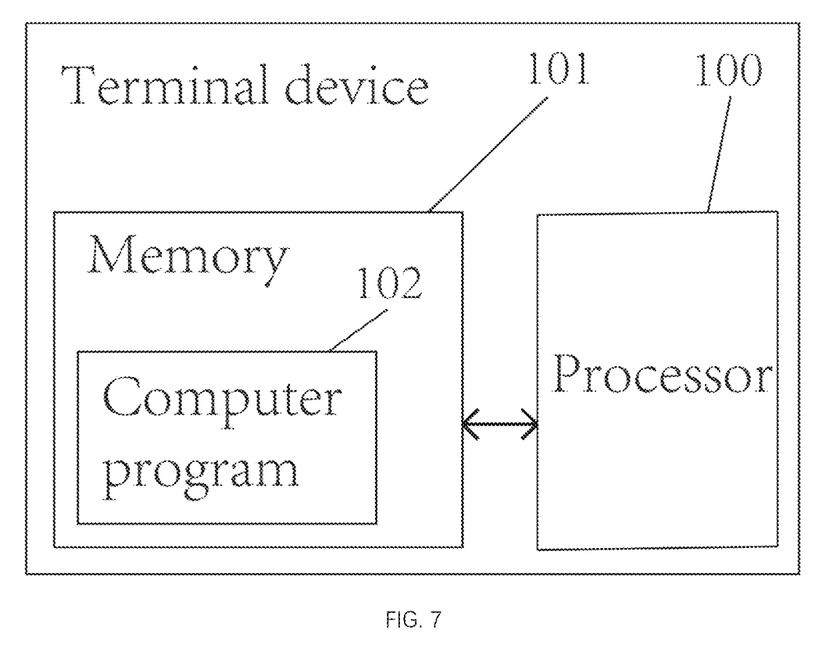
FIG. 7 is a functional block diagram of a terminal device provided by the embodiments of the present disclosure.

Based on the above embodiments, the present disclosure further provides a terminal device. A functional block diagram of the terminal device can be shown in FIG. 7. The terminal device may include one or more processors 100 (only one is shown in FIG. 7), a memory 101, and a computer program 102 stored in the memory 101 and executable on the one or more processors 100, for example, the computer program 102 may be a program for unlocking based on vein input and identification. When the one or more processors 100 execute the computer program 102, each step of the unlocking method based on vein input and identification in the above embodiments can be implemented. Alternatively, when the one or more processors 100 execute the computer program 102, the functions of each module/unit of the intelligent lock based on vein input and identification can be implemented, which is not limited here.

In one embodiment, the processor 100 may be a central processing unit (CPU), a general-purpose processor, a digital signal processor (DSP), an application specific integrated circuit (ASIC), a field-programmable gate array (FPGA) or other programmable logic devices, discrete gates, transistor logic devices, discrete hardware components, etc. The general-purpose processor may be a microprocessor or any regular processor.

In one embodiment, the memory 101 may be an internal storage unit of an electronic device, such as a hard disk or an internal memory of the electronic device. The memory 101 may also be an external storage device of the electronic device, such as a plug-in hard disk, a smart media card (SMC), a secure digital (SD) card, a flash card, etc. equipped at the electronic device. Further, the memory 101 may also include both an internal storage unit of the electronic device and an external storage device of the electronic device. The memory 101 is configured to store computer programs, and other programs and data required by the terminal device. The memory 101 may also be configured to temporarily store data that has been output or is to be output.

Those skilled in the art can understand that the functional block diagram shown in FIG. 7 is only a block diagram of a partial structure related to the technical schemes of the present disclosure, and does not constitute a limitation on the terminal device to which the technical schemes of the present disclosure are applied. Specific terminal device may include more or fewer components than shown, or combine certain components, or have a different arrangement of components.

Those ordinary skilled in the art can understand that all or part of the steps in the above method embodiments can be implemented by instructing relevant hardware through a computer program. The computer program may be stored in a non-volatile computer-readable storage medium, when the computer program is executed, the steps of the above method embodiments are implemented. Among them, any reference to memory, storage, operational database or other medium used in the embodiments provided by the present disclosure may include non-volatile and/or volatile memory. The non-volatile memory may include read-only memory (ROM), programmable ROM (PROM), electrically programmable ROM (EPROM), electrically erasable programmable ROM (EEPROM), or flash memory. The volatile memory may include a random access memory (RAM) or an external cache memory. By way of illustration and not limitation, RAM is available in many forms, such as static RAM (SRAM), dynamic RAM (DRAM), synchronous DRAM (SDRAM), dual operational data rate SDRAM (DDRSDRAM), enhanced SDRAM (ESDRAM), synchlink DRAM (SLDRAM), rambus direct RAM (RDRAM), direct rambus dynamic RAM (DRDRAM), and rambus dynamic RAM (RDRAM), etc.

In summary, the present disclosure discloses an unlocking method and an intelligent lock based on vein input and identification. The method includes: obtaining a positional information of a target part, adjusting a position of the target part to be within a preset position-identification range, inputting a vein image of the target part to be within the position-identification range, where the vein image includes a first vein image and a second vein image; processing the input first vein image to obtain a first vein feature of the first vein image, constructing a feature map based on the first vein feature; processing the input second vein image to obtain a second vein feature of the second vein image, comparing the second vein feature with the first vein feature of the feature map to obtain a comparison result, and determining an unlocking state based on the comparison result. The present embodiment can improve the security and accuracy of a user's identity authentication by using vein features as an identification basis for unlocking.

Finally, it should be noted that the above embodiments are only used to illustrate the technical schemes of the present disclosure, but not to limit them. Although the present disclosure is described in detail with reference to the foregoing embodiments, those ordinary skilled in the art should understand that: they can make modifications to the technical schemes described in the foregoing embodiments, or make equivalent substitutions to some of the technical features, however, these modifications or substitutions do not cause the essence of the corresponding technical schemes to deviate from the spirit and scope of the technical schemes of the embodiments of the present disclosure.

What is claimed is:

1. An unlocking method based on vein input and identification, the method comprising steps of:
   obtaining positional information of a target part, adjusting a position of the target part to be within a preset position-identification range, and inputting a vein image of the target part to be within the preset position-identification range, wherein the vein image comprises a first vein image and a second vein image;
   processing the input first vein image to obtain a first vein feature of the first vein image, and constructing a feature map based on the first vein feature; and
   processing the input second vein image to obtain a second vein feature of the second vein image, comparing the second vein feature with the first vein feature of the feature map to obtain a comparison result, and determining an unlocking state based on the comparison result,
   wherein the step of processing the input first vein image to obtain the first vein feature of the first vein image, and constructing the feature map based on the first vein feature, comprises steps of:
   segmenting the first vein image to divide the first vein image into a plurality of feature areas;
   extracting and calculating first vein information of each feature area, wherein the first vein information comprises a vein path position, bifurcation-point information, trend information, and ending information; and
   recording valid information of the first vein information and constructing the feature map based on the valid information.

2. The method according to claim 1, wherein the vein image of the target part is one or more of a palm vein image, a finger vein image, and/or a wrist vein image.

3. The method according to claim 1, wherein the step of obtaining the positional information of the target part, adjusting the position of the target part to be within the preset position-identification range, comprises steps of:
   receiving an input command, and collecting an original image of the target part based on the input command;
   performing a binarization processing and an edge detection on the original image to obtain an image contour of the target part in the original image, and determining a center-point position of the target part based on the image contour; and
   adjusting the position of the target part to be within the preset position-identification range based on the center-point position.

4. The method according to claim 3, wherein the step of adjusting the position of the target part to be within the preset position-identification range based on the center-point position, comprises steps of:
   dividing the preset position-identification range into a plurality of areas, and determining an area where the center-point position is located;
   based on the area where the center-point position is located, calculating area offset information of the area relative to a center of the preset position-identification range; and
   based on the area offset information, controlling an angle control unit to adjust an identification angle of an adjustable support to make the area where the center-point position is located be at the center of the preset position-identification range.

5. The method according to claim 1, wherein the step of inputting the vein image of the target part to be within the preset position-identification range, wherein the vein image comprises the first vein image and the second vein image, comprises steps of:
   reading an input mode, and determining a type of the vein image of the input target part;
   when the input mode is a registration mode, determining the vein image of the input target part as the first vein image; and
   when the input mode is an identification mode, determining the vein image of the input target part as the second vein image.

6. The method according to claim 1, wherein the step of comparing the second vein feature with the first vein feature of the feature map to obtain the comparison result, and determining the unlocking state based on the comparison result, comprises steps of:
   comparing second vein information of the second vein feature respectively with the first vein information of the first vein feature of the feature map to obtain a comparison score;
   when the comparison score is less than a preset score, controlling a latch drive unit to maintain a locked state; and
   when the comparison score is greater than the preset score, controlling the latch drive unit to unlock.

7. An intelligent lock based on vein input and identification, the intelligent lock comprising:
   a vein image input module configured to obtain positional information of a target part, adjust a position of the target part to be within a preset position-identification range, and input a vein image of the target part to be within the preset position-identification range, wherein the vein image comprises a first vein image and a second vein image;
   a feature map construction module configured to process the input first vein image to obtain a first vein feature of the first vein image, and construct a feature map based on the first vein feature; and
   an unlocking state determination module configured to process the input second vein image to obtain a second vein feature of the second vein image, compare the second vein feature with the first vein feature of the feature map to obtain a comparison result, and determine an unlocking state based on the comparison result,
   wherein the feature map construction module is further configured to segment the first vein image to divide the first vein image into a plurality of feature areas, extract and calculate first vein information of each feature area, wherein the first vein information comprises a vein path position, bifurcation-point information, trend information, and ending information, and record valid information of the first vein information and construct the feature map based on the valid information.

8. A terminal device, wherein the terminal device comprises a memory, a processor, and an unlocking program based on vein input and identification; the unlocking program is stored in the memory and executable on the processor; and when the unlocking program is executed by the processor, the steps of the unlocking method based on vein input and identification according to claim 1 are implemented.

* * * * *